(12) United States Patent
Jungnickel et al.

(10) Patent No.: US 8,656,548 B2
(45) Date of Patent: Feb. 25, 2014

(54) ORAL CLEANING SECTION OF AN ORAL CLEANING DEVICE AND ORAL CLEANING DEVICE

(75) Inventors: Uwe Jungnickel, Koenigstein/Taunus (DE); Benedikt Heil, Ober-Morlen (DE)

(73) Assignee: Braun GmbH, Kronberg (DE)

( * ) Notice: Subject to any disclaimer, the term of this patent is extended or adjusted under 35 U.S.C. 154(b) by 432 days.

(21) Appl. No.: 12/968,495

(22) Filed: Dec. 15, 2010

(65) Prior Publication Data

US 2011/0138562 A1   Jun. 16, 2011

(30) Foreign Application Priority Data

Dec. 16, 2009   (EP) .................................... 09015551

(51) Int. Cl.
    *A47K 7/02*      (2006.01)
(52) U.S. Cl.
    USPC ........... 15/221; 15/159.1; 15/176.1; 15/176.5
(58) Field of Classification Search
    USPC ............................ 15/159.1, 176.1, 176.5, 221
    See application file for complete search history.

(56) References Cited

U.S. PATENT DOCUMENTS

| 3,369,265 | A | * | 2/1968 | Halberstadt et al. | ........... 15/22.1 |
| 4,991,249 | A | | 2/1991 | Suroff | |
| 5,365,627 | A | | 11/1994 | Jousson et al. | |
| 5,617,601 | A | * | 4/1997 | McDougall | .................... 15/22.1 |
| 2004/0016067 | A1 | * | 1/2004 | Kraemer | ........................ 15/22.1 |
| 2010/0251493 | A1 | | 10/2010 | Sale et al. | |

FOREIGN PATENT DOCUMENTS

| DE | 19508932 A1 | 9/1996 |
| WO | WO00/76420 A1 | 12/2000 |

* cited by examiner

*Primary Examiner* — Lee D Wilson
*Assistant Examiner* — Shantese McDonald
(74) *Attorney, Agent, or Firm* — John P. Colbert; Vladimir Vitenberg

(57) ABSTRACT

An oral cleaning section for detachable connection with a handle section of an oral cleaning device is disclosed. The oral cleaning section has a connector structure for detachably attaching the oral cleaning section to the handle section. The connector structure has a first receptacle suitable for accommodating a first protrusion of the handle section in the attached state, the first receptacle having a first resilient element provided on a first circumferential side of the first receptacle arranged in a circumferential direction, the circumferential direction being defined with respect to the longitudinal extension axis of the oral cleaning section. The disclosure is also directed to an oral cleaning device that includes an oral cleaning section attached to a handle section.

15 Claims, 7 Drawing Sheets

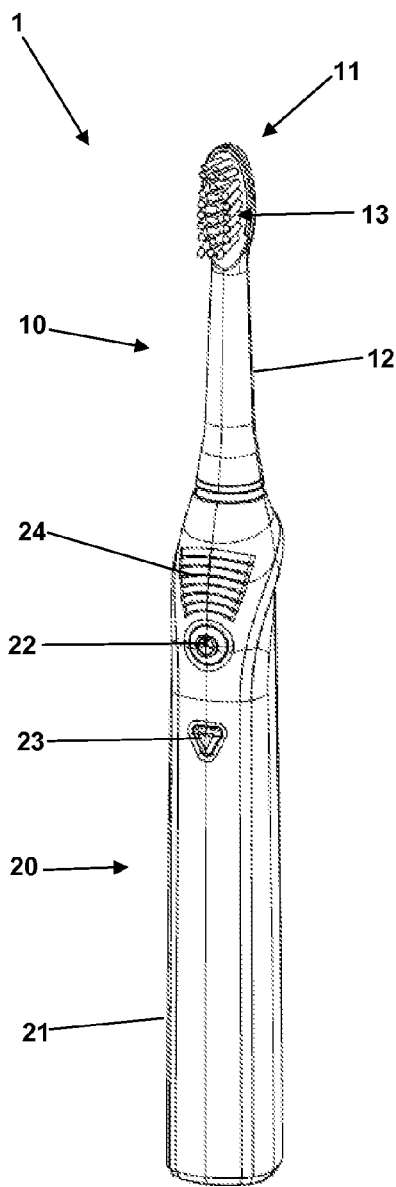
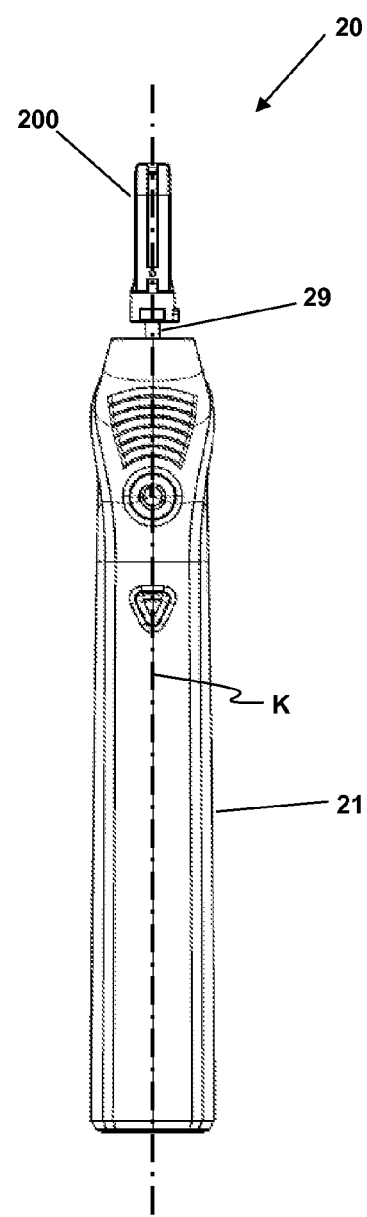
Fig. 1
Fig. 2

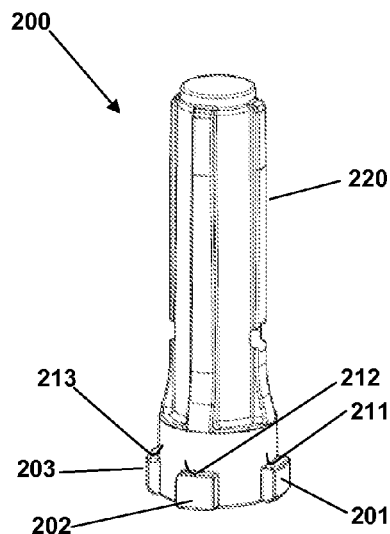
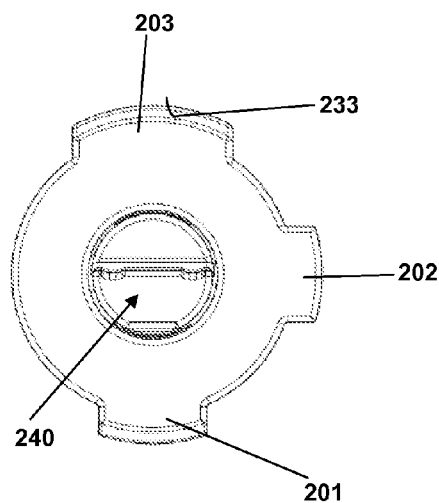
Fig. 4A                    Fig. 4B
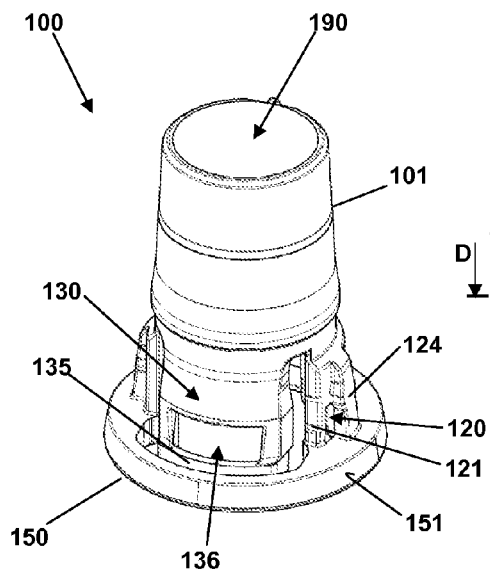
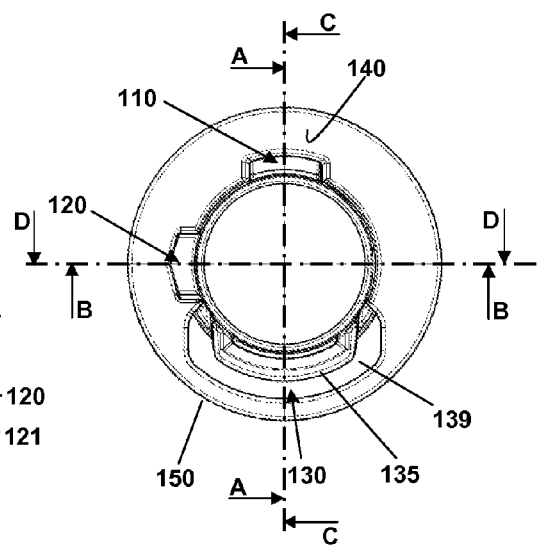
Fig. 5A                    Fig. 5B

ORAL CLEANING SECTION OF AN ORAL CLEANING DEVICE AND ORAL CLEANING DEVICE

CROSS REFERENCE TO RELATED APPLICATIONS

This application claims the benefit of European Patent Convention Application No. 09015551.6, filed Dec. 16, 2009, the substance of which is incorporated by reference in its entirety herein.

FIELD OF THE INVENTION

The present disclosure is directed to an oral cleaning section of an oral cleaning device. More particularly, the present disclosure is directed to an oral cleaning section that has a connector structure for detachably attaching the oral cleaning section to a handle section of the oral cleaning device.

BACKGROUND OF THE INVENTION

Replaceable oral cleaning sections for oral cleaning devices are widely known. Various connector structures were proposed to establish a detachable connection between an oral cleaning section and an oral cleaning device handle. For example, DE 195 08 932 A1 describes an oral cleaning device having inner and outer couplings that are formed so as to simultaneously connect to their respective parts by a turn of the oral cleaning section relative to the handle section. The outer coupling is realized as a bayonet coupling.

It is one disadvantage of the known connector structures that they have a certain play in circumferential direction due to unavoidable manufacturing tolerances, which play leads to wear of the connector structure and/or to unwanted noise during operation. It is a further disadvantage, in particular with respect to the above discussed bayonet coupling, that the coupling can get uncoupled if a certain force is applied during operation in circumferential direction, for example, when the brush head is moved from the gum to the teeth so that the bayonet coupling is eventually released, which is unwanted during operation.

Thus it is a desire to provide an oral cleaning section of an oral cleaning device that has a connector structure that has improved fixation against circumferential movement.

SUMMARY OF THE INVENTION

In one embodiment, an oral cleaning section for detachable connection with a handle section of an oral cleaning device is provided. The oral cleaning section includes a connector structure for detachably attaching the oral cleaning section to the handle section. The connector structure has a first receptacle suitable for accommodating a first protrusion of the handle section in the attached state. The first receptacle has a first resilient element provided on a first circumferential side of the first receptacle arranged in a circumferential direction, the circumferential direction being defined with respect to the longitudinal extension axis of the oral cleaning section.

In another embodiment, an oral cleaning device is provided. The oral cleaning device includes an oral cleaning section; a handle section to which the oral cleaning section is detachably connected; and a connector structure provided at either the oral cleaning section or the handle section. The connector structure has a first receptacle accommodating a first protrusion provided at the other one of the oral cleaning section or handle section in the attached state. The first receptacle has a first resilient element provided on a first circumferential side of the first receptacle in circumferential direction, the circumferential direction being defined with respect to the longitudinal extension axis of the oral cleaning section.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

FIG. 1 is a perspective view of an oral cleaning device according to one embodiment comprising an oral cleaning section and a handle section;

FIG. 2 is a frontal view onto a handle section of the oral cleaning device shown in FIG. 1;

FIG. 4A is a perspective view of a shaft part of the handle section shown in FIG. 2;

FIG. 4B is a bottom view onto the shaft shown in FIG. 4A;

FIG. 5A is a perspective view of an insert part according to one embodiment;

FIG. 5B is a bottom view of the insert part shown in FIG. 5A;

DETAILED DESCRIPTION OF THE INVENTION

Figure 3A:
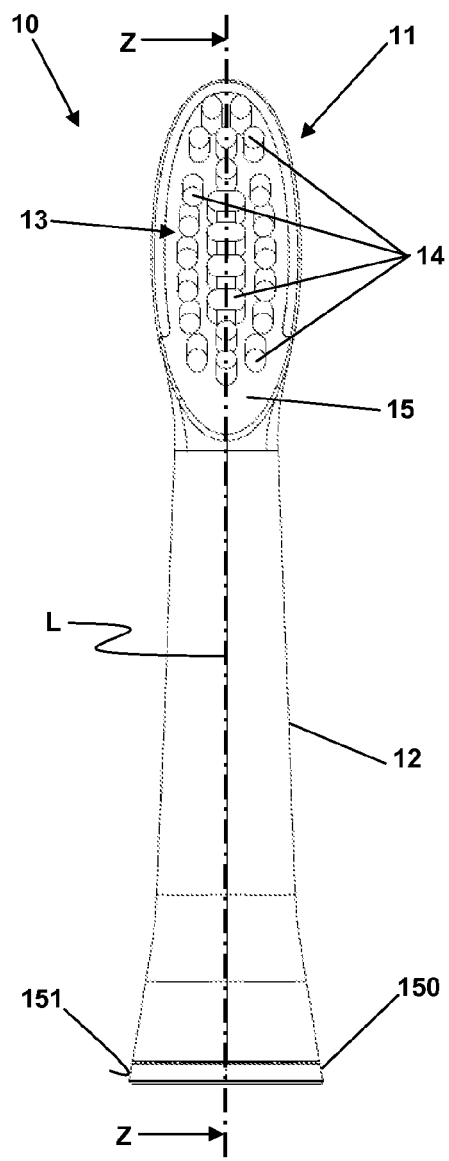
FIG. 3A is a frontal view of an oral cleaning section according to one embodiment.

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

An oral cleaning section that satisfies the mentioned desire is provided in accordance with claim 1 and an oral cleaning device comprising such an oral cleaning section is provided in accordance with claim 10. Further embodiments are provided by the dependent claims.

According to the present disclosure, an oral cleaning section is arranged for a detachable connection with a handle section of an oral cleaning device such that the oral cleaning section and the handle section form the oral cleaning device in the attached state. In one embodiment, the oral cleaning section comprises a connector structure for establishing the detachable connection with the handle section. The connector structure comprises a first receptacle suitable for accommodating a first protrusion of the handle section, where the first protrusion is in particular a radially outward extending protrusion and the first receptacle also extends radially outward and has an open bottom so that the first protrusion can slide into the first receptacle during the attachment process. The first receptacle also has a first resilient element provided on a first circumferential side of the first receptacle arranged in circumferential direction, where the circumferential direction is defined with respect to a longitudinal extension axis of the oral cleaning section. The first resilient element is realized as a clamping element (or spring element) that will act on the first protrusion in the attached state with a certain spring force, i.e. when attaching the oral cleaning section to the handle section, the first protrusion elastically deforms the resilient element in circumferential direction such that it will be circumferentially biased against the first protrusion. The first resilient element is in particular arranged as a non-snap element, i.e. the first resilient element does not provide for any snap action. Provision of the first resilient element on a first circumferential side in circumferential direction leads to a circumferential fixation, i.e. play in circumferential direction is effectively avoided such that the oral cleaning section has reduced play against any rotation around the longitudinal extension direction in the attached state as the first resilient element provides for a resilient clamping.

In an embodiment of the oral cleaning section, the connector structure has a second receptacle that is suited to accommodate a second protrusion of the handle section in the attached state. In particular, the second protrusion is a radially outward extending protrusion and the second receptacle is also radially outward extending. The second receptacle has an open bottom so that the second protrusion can slide into the second receptacle during the attachment process. The second receptacle has a second resilient element that is provided on a second circumferential side in opposite circumferential direction to the circumferential direction in which the first resilient element is provided. The second resilient element is in particular realized as a non-snap element, i.e. a resilient element that only provides for a clamping action and not for a snap-fit action. As the first and the second resilient element are thus provided in opposite circumferential direction, tolerances in the manufacture of the protrusions and the receptacles can be balanced out by the resiliency of the resilient elements and circumferential play is even better suppressed by having a first and a second resilient element. In another embodiment, the first and the second receptacle are circumferentially offset by at least 90 degrees.

In the above embodiments, it should not be excluded that the receptacles comprise further resilient elements, whether these elements are realized as clamping elements or as snap-fit elements. For example, in one embodiment, the first receptacle comprises a radially inward projecting fourth resilient element that is arranged on a radially outward lying side of the first receptacle to reduce play in the radial direction.

In another embodiment of the oral cleaning section, the connector structure comprises a third resilient element that has a snap nose suitable for snapping behind a third protrusion of the handle section in the attached state. The third protrusion is in particular radially outwards extending. In one embodiment, the third resilient element is arranged such that the snap nose can pivot radially outward from its rest position. In another embodiment, the third resilient element comprises a cutout through which the third protrusion can extend radially outward in the attached state. In particular, the cutout is dimensioned such that the third protrusion fits snugly into the cutout.

In yet another embodiment of the oral cleaning section, the connector structure is realized as an insert, which enables to manufacture even more complex geometries and to use a different material for the insert. The insert can be arranged so as to non-detachably snap to the remainder of the oral cleaning section in a respective manufacturing step. In a further embodiment, the connector structure is made from a low-friction or self-lubricating plastic material, in particular a polytetrafluoroethylene filled polyoxymethylene.

The present disclosure is also directed to an oral cleaning device comprising an oral cleaning section and a handle section, where the oral cleaning section is detachably attached to the handle section.

In one embodiment of the oral cleaning device, the oral cleaning section has a contact surface that is arranged so that in the attachment process, the contact surface is in sliding contact with an abutment surface of the first protrusion such that a rotation of the oral cleaning section around the longitudinal extension direction of the oral cleaning section is allowed until the first receptacle and the first protrusion match in position and the first protrusion slides into the first receptacle.

In another embodiment of the oral cleaning device, the handle section comprises a shaft that longitudinally extends from the handle section, which shaft comprises the first protrusion. The shaft is in particular the driving shaft for moving the oral cleaning section with respect to the handle section.

In a further embodiment of the oral cleaning device, the first protrusion is dimensioned such that it has a circumferential width that is larger than the free inner circumferential width of the first receptacle, where the free inner circumferential width is the minimal inner circumferential width measured in a plane perpendicular to the longitudinal extension axis of the oral cleaning section while the first resilient element is in a rest state. In particular, the width of the first protrusion is chosen such that the first protrusion and the first receptacle would form a transition fit if the resilient element would essentially be not resilient.

In yet a further embodiment of the oral cleaning device in which the oral cleaning section comprises a third resilient element and the handle section comprises a third protrusion as mating partner, the third resilient element is dimensioned in radial direction such that it engages the third protrusion under radial stress. This radial stress enhances the overall clamping force and reduces any angular play such that a tilting of the oral cleaning section with respect to the handle section is reduced.

The present disclosure is also directed to an oral cleaning device comprising an oral cleaning section that is detachably attached to a handle section, where one of the oral cleaning section and the handle section comprises a connector structure that has a first receptacle as has been described above and the other of the oral cleaning section and handle section comprises a first protrusion as has been described in the above. All other features as described above may also be present in such an oral cleaning device. In particular, the first protrusion may be realized at the handle section, while the second protrusion is realized at the oral cleaning section. In general, the described mating connection features may be realized in any possible way so that one of the mating connector partner (for example, a receptacle) is realized on one of the oral cleaning section and handle section, while the other mating partner (for example, a protrusion) is realized on the other one of the oral cleaning section and handle section.

Referring now to FIG. 1, there is shown a perspective depiction of an exemplary embodiment of an oral cleaning device 1, which is in the shown embodiment realized as an electric toothbrush. The oral cleaning device 1 comprises a detachable oral cleaning section 10, and a handle section 20 to which the oral cleaning section 10 is attached. The oral cleaning section 10 comprises a generally tubular neck section 12 and a head section 11. A bristle field 13 is arranged at the head section 11 so as to allow brushing of teeth in an oral cavity. In other embodiments, the oral cleaning section may, for example, be a gum massaging section or a tongue cleaning section. The handle section 20 comprises a handle part 21 that is arranged for being gripped by a user's hand. Further, a first switch 22 is arranged at the handle part 21 for switching on and off a drive arrangement of the oral cleaning device 1 to set the oral cleaning section 10 into oscillatory motion and a second switch 23 for selecting a brushing mode. In addition, a corrugated area 24 is provided for positioning the user's thumb during operation.

FIG. 2 is a frontal view onto the handle section 20 shown with the oral cleaning section 10 being detached. The handle section 20 comprises a shaft 200 for establishing the detachable connection with the oral cleaning section 10. In the shown exemplary embodiment, the shaft 200 is an injection-molded plastic part that is fixedly connected with a metal drive shaft 29 that axially extends from the handle part 21. Details of the design of the shaft 200 are further explained with reference to FIGS. 4A and 4B. The longitudinal extension axis K of the handle section 20 (which is also the longitudinal extension axis of the shaft 200) is shown.

FIG. 3A is a frontal view onto the oral cleaning section 10 shown in a detached state. The oral cleaning section 10 comprises a generally tubular neck section 12 that is essentially hollow so as to be able to accommodate the shaft 200 shown in FIG. 2. As will be explained in more detail with reference to FIG. 3B, a connector structure 100, which in the present embodiment is shown as an insert that is fixedly connected to the inside of the hollow inner part of the neck section 12, is provided for establishing a detachable connection with the shaft 200. The head section 11 comprises a bristle field 13 which in turn comprises a plurality of bristle tufts 14 that are mounted on a bristle carrier structure 15. In the shown example (as can be seen from FIG. 3B), the bristle carrier structure 15 is slightly concave. The longitudinal extension axis L of the oral cleaning section 10 is indicated by a dashed-dotted line.

Figure 3B:
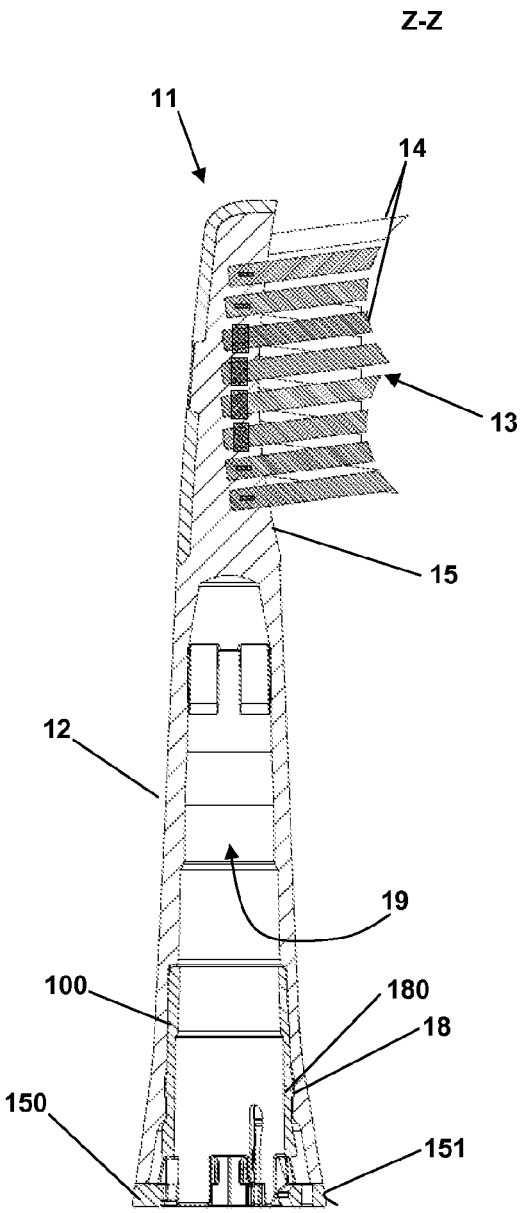
FIG. 3B is a cross sectional cut of the oral cleaning section as shown in FIG. 3A taken along line Z-Z.

Referring now to FIG. 3B, there is shown a longitudinal cut through the oral cleaning section 10 along line Z-Z indicated in FIG. 3A. The oral cleaning section 10 comprises a head section 11 and a neck section 12. The head section 11 comprises a bristle field 13 having a plurality of bristle tufts 14 (in another embodiment, further tooth cleaning elements such as tooth polishing elements or gum massaging elements such as soft elastomeric fingers may be arranged as part of the bristle field or alternately to the bristle tufts) mounted on the bristle carrier structure 15 that in the shown embodiment is slightly concave in the longitudinal extension direction of the oral cleaning section 10. The neck section 12 is of a generally tubular design having a hollow inner cavity 19 that is open towards the end of the neck section 12 that is distal to the head section 11. A connector structure 100 is realized as an insert that is fixedly connected inside the hollow cavity 19 at the open end of the neck section 12 such that the connector structure 100 concludes the oral cleaning section 10 with a ring structure 150. The insert may be manufactured independently from the remainder of the neck section 12, which in particular allows using a different material for the connector structure 100, specifically a material having low wear properties. In the manufacturing process, the insert is inserted into the hollow cavity 19 formed in the neck section 12 where the insert will establish an essentially inseparable connection with the neck section 12 via one or several complementing 90 degree undercuts 180 and 18 provided on the outside of the insert and the inside of the neck section 12, respectively. The shaft 200 of the handle section 20 shown in FIG. 2B can be introduced into the hollow cavity 19 such that the connector structure 100 establishes a detachable connection with the shaft 200 in the attached state as will be explained in the following. The ring structure 150 has a radial outer surface 151 that concludes the outer surface of the neck section 12. Different inserts may be made from differently colored materials to allow differentiating different oral cleaning sections 10, for example, for identifying a personal oral cleaning section if a handle section is used by different users with different oral cleaning sections. In another embodiment, the connector structure 100 is an integral part of the neck section 12, for example, manufactured in a single molding process.

FIG. 4A is a perspective view onto the shaft 200 that is shown in FIG. 2 as a part of the handle section 20. The shaft 200 comprises an elongated shaft element 220, which in the shown embodiment has a generally cylindrical form and which in an attached state extends into the hollow cavity 19 of the oral cleaning section 10 shown in FIG. 3B. In particular, the elongated shaft element 220 and the hollow cavity 19 may be designed so that they establish a transition fit in an area proximal the head section 11 for supporting an essentially play-free connection of the oral cleaning section 10 with the handle section 20. The shaft 200 further comprises a first protrusion 201, a second protrusion 202, and a third protrusion 203 that extend radially outward from the elongated shaft element 220. The first protrusion 201 has an abutment surface 211, the second protrusion 202 has an abutment surface 212, and the third protrusion 203 has an abutment surface 213. The abutment surfaces 211, 212, and 213 of the protrusions 201, 202, 203 all lie in a plane that is perpendicular to the longitudinal extension axis K (as indicated in FIG. 2) of the shaft 200. As will be explained in more detail below with reference to FIGS. 7A and 7B, the abutment surfaces 211, 212, and 213 provide for a sliding contact of a contact surface of the connector structure 100 such that free rotation of the oral cleaning section 10 around the longitudinal extension axis K is allowed until the protrusions 211, 212, and 213 coincide in position with respective receptacles of the connector structure 100. In the attached state, the longitudinal extension axis L of the oral cleaning section 10 and the longitudinal extension axis K of the handle section 20 coincide. The lower surfaces of the protrusions 201, 202, and 203 flush with the lower surface of the elongated shaft element 220. In other embodiments, the shaft 200 (or more generally: the handle section 20) may comprise only a single protrusion such as the first protrusion 201 or may comprise two protrusions such as only the first and the second protrusion 201 and 202 or only the first protrusion 201 and the third protrusion 203. In an even further embodiment, the handle section 20 may comprise four protrusions or even more.

FIG. 4B is a bottom view onto the lower surface of the shaft 200 (where the bottom of the shaft 200 is the side that is proximal the handle section 20). The protrusions 201, 202 and 203 extend radially outward from the circular main body of the shaft 200. The second protrusion 202 is arranged with a 90 degrees circumferential offset (in counter-clockwise direction when seen onto the bottom of the shaft 200) to the first protrusion 201 and the third protrusion 203 is arranged with a 90 degrees circumferential offset to the second protrusion 202. The three protrusions 201, 202, and 203 are realized having different widths in circumferential direction. The positional arrangement and the different widths support that only a single connecting position between the connector structure 100 and the shaft 200 is provided even if the user would try to push the oral cleaning section 10 onto the handle section 20 with a certain force.

FIG. 5A is a perspective view onto the connector structure 100 that in the present embodiment is realized as an insert as has been explained above. The connector structure may be realized by an injection molding process using a suitable plastic material such as polyoxymethylene (POM), in particular a polytetrafluoroethylene (PTFE) filled POM for low wear properties of the connector structure 100 (such wear may in particular occur if oral cleaning additives such as toothpaste are used that contain abrasive particles). The connector structure 100 has a hollow, essentially cylindrical main body 101. A first receptacle 110 (which is depicted specifically in FIG. 6B) may include a cylindrical main body 101 opposite to a third resilient element 130. The third resilient element 130 may include a resilient snap arm that is in particular arranged such that a snap nose part 135 provided at a free end of the resilient snap arm can pivot radially outwards if a radially outward directed force acts on the snap nose. The third resilient element 130 includes a cutout 136 that is dimensioned that that it can accommodate the third protrusion 203 while the snap nose part 135 will snap essentially under the third protrusion 203 in the attached state, as will be explained further below. Further, a second receptacle 120 includes the hollow cylindrical main body 101 with a 90 degrees offset between both, the first receptacle 110 and the third resilient element 130 so that the position and the width of the two receptacles 110 and 120 and of the pivotably arranged third resilient element 130 coincide with the three protrusion 201, 202, and 203 of the shaft 200 such that attachment of the oral cleaning section 10 onto the handle section 20 is enabled. A bar structure 124 is arranged at a radially outward position in the middle of the second receptacle 120. The connector structure 100 has a circular bottom ring structure 150 that extends radially outward from the hollow cylindrical main body 101. In an attached state, a radially outer surface 151 of the ring structure 150 concludes the outer surface of the neck section 12 (as was discussed with reference to FIG. 3B).

FIG. 5B is a bottom view onto the connector structure 100 (where the bottom is defined as the end surface that lies distal to the head section when the connector structure is attached to the neck section 12). The connector structure 100 comprises the first receptacle 110, the second receptacle 120 that is arranged with a counter-clockwise 90 degree offset in circumferential direction to the first receptacle 110 when seen onto the bottom side, and the third resilient element 130 that is arranged with a counter-clockwise 90 degree offset in circumferential direction to the second receptacle 120. The first and second receptacles 110 and 120 are open at the bottom so that the first and second protrusions 201 and 202 can easily slide into the first and second receptacles 110 and 120, respectively, when the oral cleaning section 10 is attached onto the handle section 20 (as will be explained in more detail below with reference to FIGS. 7A, 7B, 8A, and 8B). The ring structure 150 comprises a planar contact surface 140 that lies in a plane perpendicular to the longitudinal extension axis (which coincides with axis L shown in FIG. 3A) of the insert. A cutout 139 extending radially outwards is provided in the ring structure 150 to allow for a radially outward movement of the snap-nose part 135 of the third resilient element 130, where the third resilient element 130 is realized as a snap arm having at a free end the snap-nose part 135, which snap-nose part 135 comprises a radially inwards projecting snap nose.

Figure 6A:
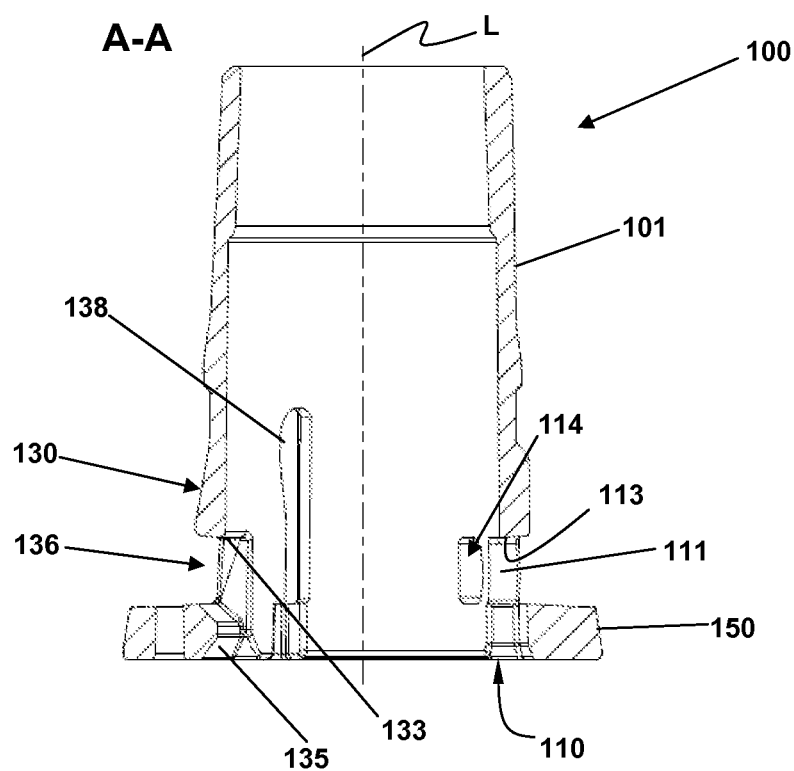
FIG. 6A is an open cut view onto an inner side of the insert part shown in FIG. 5A, where the cut is taken along line A-A indicated in FIG. 5B and having the indicated viewing direction.

Referring now to FIG. 6A, there is shown a longitudinal open cut through the connector structure 100 along line A-A as indicated in FIG. 5B with the respective viewing direction indicated by arrows. The cut crosses through the first receptacle 110 and the third resilient element 130. The first receptacle 110 comprises a first resilient element 111 provided on a first circumferential side that extends in circumferential direction into the first receptacle 110. In one embodiment, the first resilient element 111 is a relatively thin wall element made during the injection molding process by which the whole insert is realized. Being thin and made of a plastic material, the first resilient element 111 can elastically deform when the first protrusion 201 is slid into the first receptacle 110 during the attachment process. Due to spring forces, the first resilient element 111 then clamps the first protrusion 201, as will be explained further with reference to FIG. 6B. In one embodiment, the third resilient element 130 is a snap arm comprising a cutout 136 realized in the snap arm above the snap nose part 135. The cutout 136 in the snap arm is dimensioned such that the third protrusion 203 can extend through the cutout in the attached state.

Figure 6B:
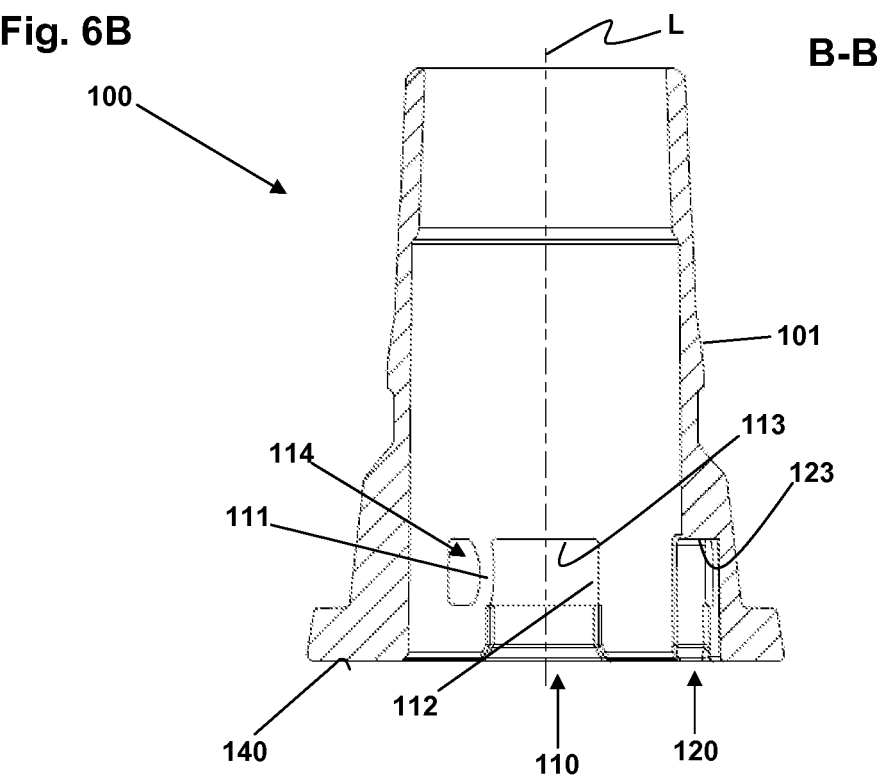
FIG. 6B is an open cut view onto an inner side of the insert part shown in FIG. 5A, where the cut is taken along line B-B indicated in FIG. 5B and having the indicated viewing direction.

FIG. 6B is a longitudinal open cut through the connector structure 100 along line B-B as indicated in FIG. 5B with the respective viewing direction indicated by arrows. The first receptacle 110 is open at the bottom end to allow for receiving the first protrusion 201 during the attachment process. The first receptacle 110 comprises a first side wall 112, a first top wall 113 and—provided on a first circumferential side—the first resilient element 111 realized as a relatively thin wall segment that is curved such that it projects in circumferential direction into the first receptacle 110. A cutout 114 is provided in the hollow cylindrical main body 101 of the connector structure 100 to allow bending of the first resilient element 111 in circumferential direction opposite to its extension direction into the cutout 114. During the attachment process, the first protrusion 201 slides into the first receptacle 110. The circumferential dimension of the first protrusion 201 is designed to be slightly larger than the free minimal circumferential distance between the first resilient element 111 and the first side wall 112. The free minimal circumferential distance is the distance measured in a plane perpendicular to the longitudinal extension axis L between the first side wall 112 and the point of the first resilient element 111 that projects furthest into the first receptacle 110. E.g. the circumferential dimension of the first protrusion 201 can be designed to be from about 20 μm to about 100 μm wider than the free minimal distance between the first resilient element 111 and the first side wall 112. The tolerance on all dimensions may be such that the first protrusion and the first receptacle would generally realize a transition fit close to the crossing over to an interference fit. Here, the first resilient element 111 is on purpose provided as a spring element that is pushed into a loaded position (in which the first resilient element 111 is under stress) in the attached state and which is reversibly adopting its rest position in the detached state. In the attached state, the first resilient element 111 applies a certain pressure in circumferential direction against the first protrusion 201 so that a radial play between the oral cleaning section 10 and the handle section 20 in the attached state is effectively avoided. In another embodiment, the first resilient element is a curved projection that circumferentially extends into the first receptacle and that is made from soft elastomeric material. The soft elastomeric projection may be resiliently deformed and/or compressed in the attachment process such that the soft elastomeric projection also applies a certain force onto the first protrusion. The soft elastomeric projection may be applied in a two-component injection molding process.

Figure 6C:
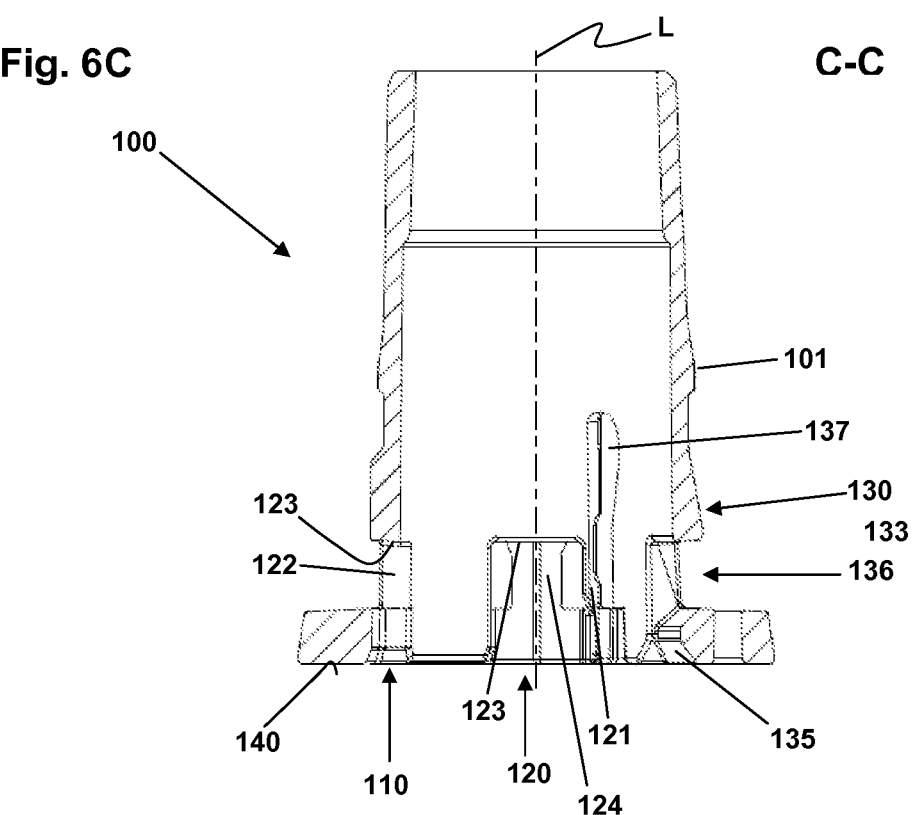
FIG. 6C is an open cut view onto an inner side of the insert part shown in FIG. 5A, where the cut is taken along line C-C indicated in FIG. 5B and having the indicated viewing direction.

FIG. 6C is a longitudinal open cut through the connector structure 100 along line C-C as indicated in FIG. 5B with the respective viewing direction indicated by arrows. A view onto the second receptacle 120 is provided. The second receptacle 120 is open at the bottom end to allow for receiving the second protrusion 202 during the attachment process. The second receptacle 120 is defined by a second side wall 122, a second top wall 123 and a second resilient element 121. In one embodiment, the second resilient element 121 is a relatively thin wall segment that partially projects into the first receptacle 110. A lateral cutout 137 of the third resilient element 130 (see FIG. 6D for details) is provided such that the second resilient element 121 can deform in circumferential direction into the thus provided clearance. In the present embodiment, in which two receptacles are provided, the second resilient element 121 is provided in the second receptacle 120 on a second circumferential side that lies in the circumferential direction opposite to the circumferential direction in which the first resilient element 111 is provided in the first receptacle 110. For example, if the first resilient element 111 is provided in counterclockwise direction, then the second resilient element 121 is provided in clockwise direction. The provision of the first and second resilient elements 111 and 121 in opposite circumferential directions serves to balance any manufacturing tolerances and to allow for effective clamping of the first and second protrusions 201 and 202 in the first and second receptacles 110 and 120, respectively.

Figure 6D:
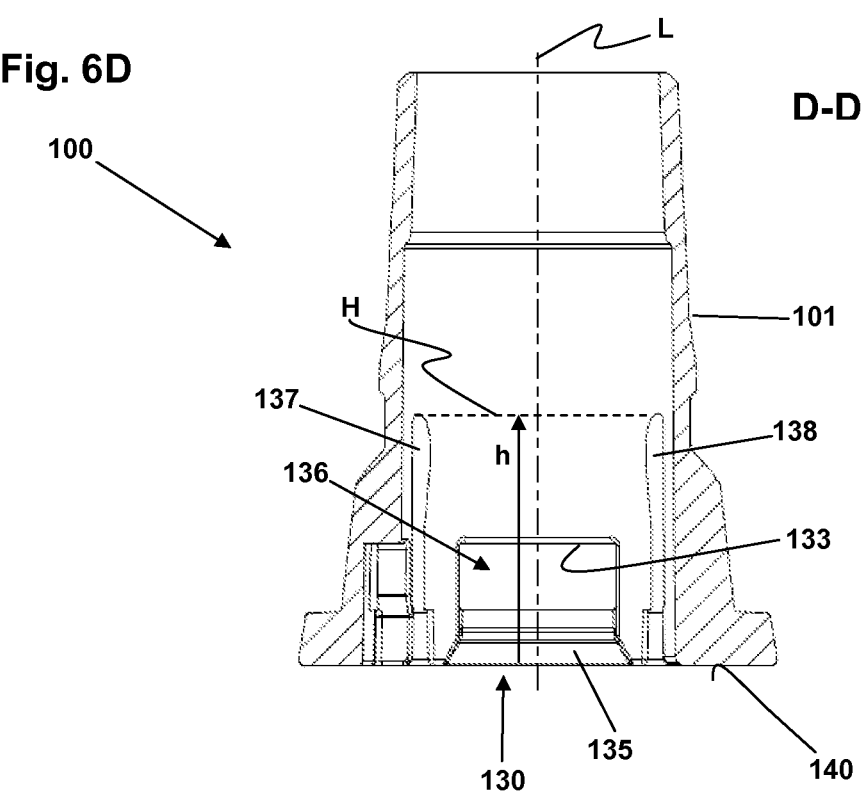
FIG. 6D is an open cut view onto an inner side of the insert part shown in FIG. 5A, where the cut is taken along line D-D indicated in FIG. 5B and having the indicated viewing direction.

FIG. 6D is a longitudinal open cut through the connector structure 100 along line D-D as indicated in FIG. 5B with the respective viewing direction indicated by arrows. In this view, the third resilient element 130 is seen. The third resilient element 130 is arranged between two lateral cutouts 137 and 138 that are provided in the hollow cylindrical main body 101 and that extend from the bottom to a certain height h. Due to these two lateral cutouts 137 and 138, a resilient tongue or arm is defined that can pivot radially outwards, where a line H connecting the two top corners of the lateral cutouts 137 and 138 essentially represents the hinge for the radial outwards pivoting. The third resilient element 130 comprises a snap nose part 135 at the free bottom end of the third resilient element 130. The snap nose part 135 has a snap nose that extends radially inwards. The snap nose has a chamfered top and bottom surface to allow for releasable snapping action. The third resilient element 130 follows the outer curvature of the hollow cylindrical main body 101 (i.e. the third resilient element 130 extends along a circular segment). Further, a cutout 136 is provided in the third resilient element 130 above the snap nose part. The cutout 136 is dimensioned to accommodate the third protrusion 203 of the shaft 200 in the attached state. As the third protrusion 203 would then extend through the cutout 136, a realization of the third resilient element 130 having low construction volume is achieved. The cutout 136 has a third top wall 133 against which the snap nose part 135 will push the abutment surface 213 of the third protrusion in the attached state (which is shown in FIG. 8A).

Figure 7A:
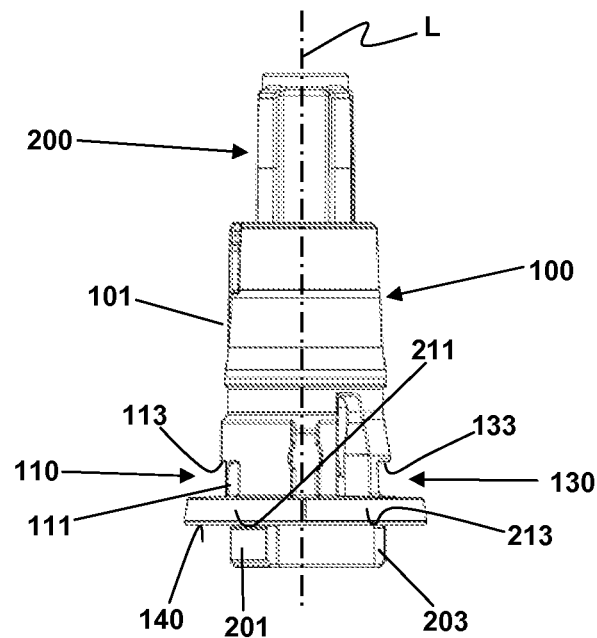
FIG. 7A is a side view onto the insert part and the shaft part in an intermediate attached state in which a contact surface of the insert part is in sliding contact with abutment surfaces provide at protrusions of the shaft part.

FIG. 7A is a side view onto the connector structure 100 and the shaft 200 in an intermediate step during the attachment process. The remainder of the oral cleaning section and of the handle section is not shown for sake of clarity. In order to attach the oral cleaning section onto the handle section, the shaft 200 was inserted into the hollow cavity formed in the neck section of the oral cleaning section. The position of the receptacles 110 and 120 and the third resilient element 130 and of the protrusions 201, 202, and 203 is not aligned so that in this intermediate position the contact surface 140 of the connector structure 100 and the abutment surfaces 211, 212, and 213 of the protrusions are in sliding contact with each other. In this position, the connector structure 100 can be freely rotated around the longitudinal extension axis L at an axial position defined by the contact plane of the contact surface 140 of the connector structure 100 and of the abutment surfaces 211, 212, and 213 of the protrusions 201, 202, and 203.

Figure 7B:
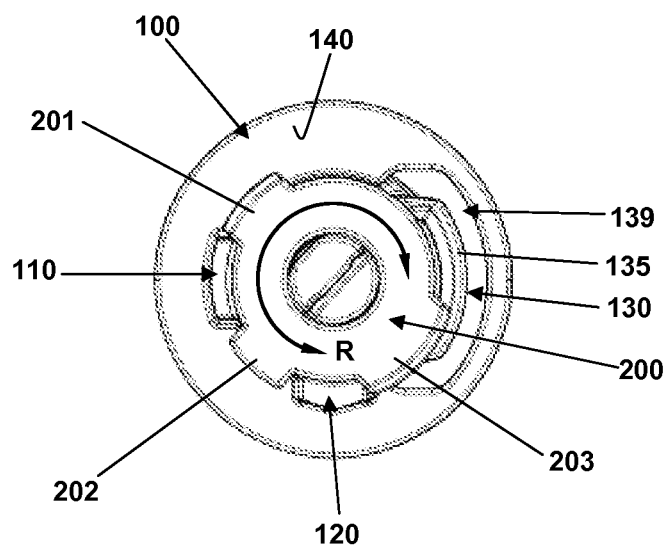
FIG. 7B is a bottom view onto the shaft part and the insert part as shown in FIG. 7A.

FIG. 7B is a bottom view onto the connector structure 100 and the shaft 200 in the intermediate attachment step as shown in FIG. 7A. At least one of the abutment surfaces of the protrusions 201, 202, 203 is always in contact with the contact surface 140 as long as the protrusions 201, 202, and 203 are not aligned in circumferential position with the receptacles 110 and 120 and the third resilient element 130. Due to the different sizes, the user can attach the connector structure 100 to the shaft 200 only in one aligned position so that it is assured that the bristle field of the head section is always aligned with the front side of the oral cleaning device.

Figure 8A:
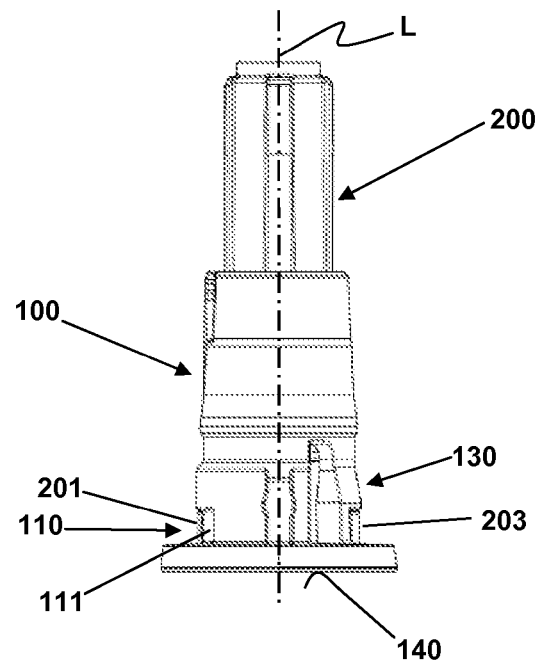
FIG. 8A is a side view onto the insert part and the shaft part in the final attached state.

FIG. 8A is a side view onto the connector structure 100 and the shaft 200 in the attached state. In order to arrive at the attached state, the user has to turn the connector structure 100 around the longitudinal extension axis L while being in the intermediate position shown in FIGS. 7A and 7B until positional alignment between the receptacles and the protrusions is achieved, which can be noticed by the user due to a tactile latching. By simply pushing the connector structure 100 and shaft 200 onto each other, the first and second protrusions 210 and 202 glide into the first and second receptacles 110 and 120, respectively, and the third protrusion 203 pivots the third resilient element 130 radially outwards until the snap nose of the snap nose part 135 snaps behind the third protrusion 203 and the third protrusion 203 moves into the cutout 136 provided in the third resilient element 130. In the attached position, the snap nose part 135 abuts the chamfered surface 233 of the third protrusion 203 under pre-stress (i.e. the third resilient element 130 has not reached its rest position but remains in a position in which it is slightly moved radially outwards) to minimize play between the oral cleaning section and the handle section.

Figure 8B:
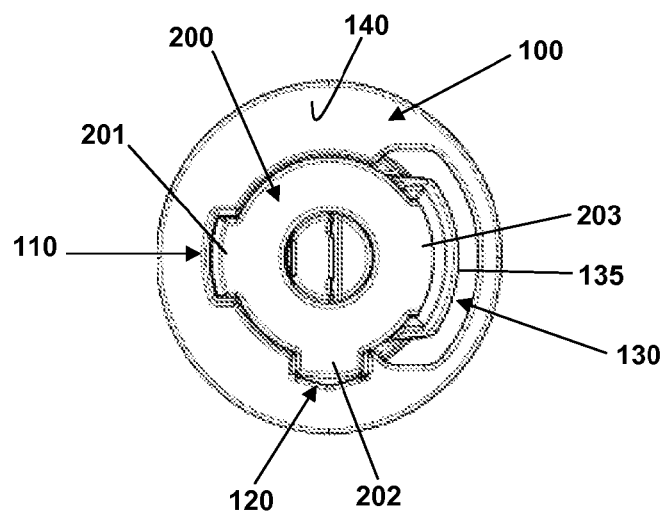
FIG. 8B is a bottom view onto the attached insert part and shaft part as shown in FIG. 8A.

FIG. 8B is a bottom view onto the connector structure 100 and the shaft 200 in the attached position as shown in FIG. 8A. The first protrusion 201 is accommodated by the first receptacle 110 and the second protrusion 202 is accommodated by the second receptacle 120. As has been explained above with reference to FIGS. 6B and 6C, the first and second resilient elements 111 and 121 that are each arranged in opposite circumferential direction on first and second circumferential sides in the first and second receptacles 110 and 120, respectively, clamp the first and second protrusions 201 and 202 in the circumferential direction so that minimized circumferential play is achieved. The third protrusion 203 is clamped by the third resilient element that remains under pre-stress such that the abutment surface 213 of the third protrusion is pushed against the top wall 133 of the cutout 136 provided in the third resilient element 130. Due to the chamfered surface 233, any tolerances in the various elements can be neglected and the third protrusion 203 is relatively tightly clamped in axial direction to avoid any axial play. In general it is to be noted that the protrusions 201, 202, and 203 could be provided at the oral cleaning section 10, while the receptacles 110 and 120 and the third resilient element 130 are provided at the handle section 20 or the protrusions may be alternately provided at the handle section 20 and the oral cleaning section 10, while the receptacles 110 and 120 and the third resilient element 130 may alternatively, be provided at the other one of the handle section 20 and the oral cleaning section 10.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral cleaning section for detachable connection with a handle section of an oral cleaning device, comprising:
a connector structure for detachably attaching the oral cleaning section to the handle section, wherein the connector structure has a first receptacle suitable for accommodating a first protrusion of the handle section in the attached state, the first receptacle having a first resilient element provided on a first circumferential side of the first receptacle arranged in a circumferential direction, the circumferential direction being defined with respect to the longitudinal extension axis of the oral cleaning section, wherein the connector structure comprises at least a third resilient element comprising a snap nose suitable for being snapped behind a third protrusion of the handle section in the attached state.

2. The oral cleaning section according to claim 1, wherein the connector structure has a second receptacle suitable for accommodating a second protrusion of the handle section in the attached state, wherein the second receptacle has a second resilient element provided on a second circumferential side of the second receptacle that is oppositely arranged to the circumferential direction in which the first resilient element is provided.

3. The oral cleaning section according to claim 2, wherein the first receptacle and the second receptacle are circumferentially offset by at least about 90 degrees.

4. The oral cleaning section according to claim 1, wherein the third resilient element is arranged such that at least the snap nose part can pivot radially outward from its rest position.

5. The oral cleaning section according to claim 1, wherein the third resilient element comprises a cutout that is suitable such that the third protrusion can extend into the cutout in the attached state.

6. The oral cleaning section according to claim 1, wherein the connector structure is an insert.

7. The oral cleaning section according to claim 1, wherein the first receptacle comprises a radially inwards projecting fourth resilient element arranged on a radially outward lying side of the first receptacle.

8. The oral cleaning section according to claim 1, wherein the connector structure is made of a low friction or self-lubricating plastic, in particular made of polytetrafluoroethylene filled polyoxymethylene.

9. Oral cleaning device comprising an oral cleaning section according claim 1 and a handle section onto which the oral cleaning section is detachably attached.

10. The oral cleaning device according to claim 9, wherein the connector structure has a contact surface extending in a plane perpendicular to the longitudinal extension axis that is arranged so that during the attachment process the contact surface gets into contact with an abutment surface of the first protrusion such that the oral cleaning section can be rotated around the longitudinal extension axis while the contact surface stays in sliding contact with the abutment surface until the first protrusion matches in position with the first receptacle.

11. The oral cleaning device according to claim 9, wherein the handle section comprises a shaft that extends along the longitudinal extension axis from the handle section and the shaft comprises the first protrusion.

12. The oral cleaning device according to claim 9, wherein the first protrusion is dimensioned in the circumferential direction such that it has a larger circumferential extension than the free circumferential inner dimension of the first receptacle, in particular wherein the first protrusion and the first receptacle form a transition fit in the attached state.

13. The oral cleaning device according to claim 9, wherein the third protrusion is dimensioned in radial direction such that the third resilient element engages the third protrusion in the attached state under radial pre-stress.

14. An oral cleaning device comprising:
an oral cleaning section;
a handle section to which the oral cleaning section is detachably connected; and
a connector structure provided at either the oral cleaning section or the handle section, which connector structure has a first receptacle accommodating a first protrusion provided at the other one of the oral cleaning section or handle section in the attached state, the first receptacle having a first resilient element provided on a first circumferential side of the first receptacle in circumferential direction, the circumferential direction being defined with respect to the longitudinal extension axis of the oral cleaning section, wherein the connector structure further comprises at least a third resilient element comprising a snap nose suitable for being snapped behind a third protrusion of the handle section in the attached state.

15. An oral cleaning section for detachable connection with a handle section of an oral cleaning device, comprising:
a connector structure for detachably attaching the oral cleaning section to the handle section, wherein the connector structure has a first receptacle suitable for accommodating a first protrusion of the handle section in the attached state, the first receptacle having a first resilient element provided on a first circumferential side of the first receptacle arranged in a circumferential direction, the circumferential direction being defined with respect to the longitudinal extension axis of the oral cleaning section, wherein the first receptacle comprises a radially inwards projecting fourth resilient element arranged on a radially outward lying side of the first receptacle.

* * * * *